United States Patent

Rebuffat

Patent Number: 6,123,663
Date of Patent: Sep. 26, 2000

[54] SURGICAL APPLIANCE FOR THE TREATMENT OF PULMONARY EMPHYSEMA

[76] Inventor: Carlo Rebuffat, Via Canova, 27-Milan, Italy

[21] Appl. No.: 09/214,157

[22] PCT Filed: Apr. 7, 1997

[86] PCT No.: PCT/IT97/00159

§ 371 Date: Dec. 23, 1998

§ 102(e) Date: Dec. 23, 1998

[87] PCT Pub. No.: WO98/01084

PCT Pub. Date: Jan. 15, 1998

[30] Foreign Application Priority Data

Jul. 4, 1996 [IT] Italy .................. MI96A1375

[51] Int. Cl.[7] .................. A61F 2/00
[52] U.S. Cl. .................. 600/37
[58] Field of Search .................. 600/37, 897, 898

[56] References Cited

U.S. PATENT DOCUMENTS 4,633,873  1/1987  Dumican et al. .................. 128/334 R
5,011,493  4/1991  Belykh et al. .................. 606/215

FOREIGN PATENT DOCUMENTS

0349505A2  1/1990  European Pat. Off. ........ A61L 27/00
0719527A1  7/1996  European Pat. Off. ........ A61F 2/00

*Primary Examiner*—Max Hindenburg
*Assistant Examiner*—Brian Szmal
*Attorney, Agent, or Firm*—Michael Best & Friedrich LLP

[57] ABSTRACT

Surgical appliance for the treatment of pulmonary emphysema consisting of a sheath (1) made up of a biocompatible elastic material provided with a hole (4) suitable for the passage of the bronchia and vessels of the lung onto which the sheath (1) is to be applied. Once applied onto the lungs of an emphysematous, the surgical appliance according to the present invention remarkably improves his breathing functionality without resorting to traumatic surgical operations, such as for instance the partial removal or the plication of the pulmonary parenchyma.

4 Claims, 1 Drawing Sheet

SURGICAL APPLIANCE FOR THE TREATMENT OF PULMONARY EMPHYSEMA

DESCRIPTION

The present invention relates to a surgical appliance for the treatment of pulmonary emphysema, and in particular to a surgical appliance which, once applied onto the lungs of an emphysematous, remarkably improves his breathing functionality without resorting to traumatic surgical operations, such as for instance the partial removal or the plication of the pulmonary parenchyma.

It is acknowledged that pulmonary emphysema has always been considered a disease that mainly, if not exclusively, relates to internal medicine and pneumology. The medical therapy of pulmonary emphysema, based upon breathing rehabilitation and use of specific medicines, is effective both as a therapeutic approach and in the preparation for a possible surgical operation. Surgery of pulmonary emphysema, preferably based upon bullectomy and pulmonary transplant, has had so far an absolutely secondary role in the therapy of this disease.

Recently Cooper has instead proposed, with great success, a surgical operation that revolutionizes the treatment of pulmonary emphysema thereby resuming a procedure developed by Brantigan in 1959 and forgotten for many years. This operation, known as lung volume reduction, consists of a reduction of the volume occupied by the emphysematous lung through surgically removing 20 to 25% of the total mass of parenchyma, in particular its functionally hypoactive peripheral areas. While the lung volume reduction seems to be illogical for the treatment of patients affected by breathing insufficiency, this kind of operation is based upon precise physiopathological fundamentals which justify the execution and the good clinical results. Indeed, the lung with a reduced volume exerts a higher elastic retraction force against the thoracic cage, thereby improving both the volumetric balance of the lung/thoracic cage system and the efficiency of the inspiratory muscles. Such an improvement is due to the fact that the emphysematous lung, less elastic than a healthy lung, tends to expand more than the usual, especially in the apical areas, causing the expansion of the thoracic cage, which is no longer subject to the elastic retraction force of the lung.

The surgical operation for the lung reduction is carried out with the assistance of linear suturing devices which automatically section the pulmonary tissue and suture it by means of metal clamps. However, the quality of such a suture, with respect to haemostasis and aerostasis, is frequently insufficient because of the fragility of the tissue altered by emphysema. Recent proposals recommend the interposition of stripes of bovine pericardium between the clamps and the pulmonary parenchyma in order to reduce the traumatic effect of the suture. The latter measure does not however eliminate the postoperatory complications such as hemorrhage and copious air losses from the sectioned and sutured pulmonary parenchyma, which often confine the patient to extensive hospitalization periods.

To reduce the frequency and the gravity of said complications it has been proposed, as an alternative to said pulmonary parenchyma partial removal technique, the plication-suture technique by means of linear suturing devices with bladeless clamps. However, such a technique cannot be performed at all times and presently there is no sufficient information confirming its effective validity.

Therefore, object of the present invention is to provide a surgical appliance for the treatment of pulmonary emphysema which reduces the volume of the emphysematous lungs without resorting to traumatic surgical operations, such as the partial removal or the plication of the pulmonary parenchyma. Said object is achieved by means of a surgical appliance whose features are disclosed in claim 1.

Thanks to the surgical appliance according to the present invention, it is possible to restore elasticity in the pulmonary parenchyma, thereby opposing the emphysematous hyperexpansion as well as helping the recovery of the physiological partial retraction state of the thoracic cage.

Moreover, the surgical operation for applying the surgical appliance according to the present invention has little traumatic effects and can be easily carried out even by means of a video-endoscopic technique, thereby without resorting to a sternotomic operation which, in this kind of patients, increases the postoperatory pain and extends the hospitalization.

Another advantage of the surgical appliance according to the present invention is due to the compression action exerted onto the pulmonary parenchyma which appears almost exclusively on the peripheral mantle and on the apical areas of the lung, that is to say, on those areas which are substantially inactive in the emphysematous with respect to the pulmonary ventilation.

Further advantages and features of the surgical appliance according to the present invention will become clearer to those skilled in the art through the following detailed description of an embodiment thereof with reference to the attached drawings wherein.

Figure 1:
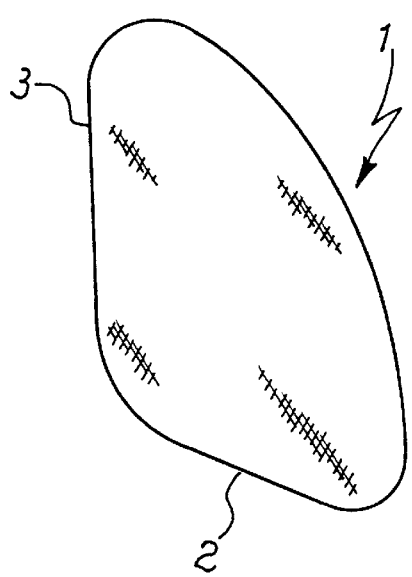
FIG. 1 shows a frontal view of the surgical appliance according to the present invention.

Referring to FIG. 1, it can be noticed that the surgical appliance according to the present invention essentially consists of a sheath 1 made up of an elastic and permeable material. Such a material may be for example a tissue knitted or processed in another way suitable for conferring to the resulting tissue a remarkable degree of both longitudinal and transversal elasticity. Such a tissue should be produced using biocompatible and hypoallergenic yarns having their own particular elasticity. They may not even be elastic when the structure of the tissue is sufficiently elastic in itself. As well, sheath 1 may be produced with an impermeable material even though this option is to be avoided in order to keep the possibility of draining air, liquids or blood residuals, if any, collected between the lung and the sheath. As a matter of fact, it serves to contain the whole pulmonary parenchyma and to control its expansion, whereby its shape should preferably follow, obviously in a simplified manner, the shape of a lung, that is, it should have a substantially ovoid shape flat at the base 2 and on the side 3 corresponding to the mediastinal face of the lung.

Figure 2:
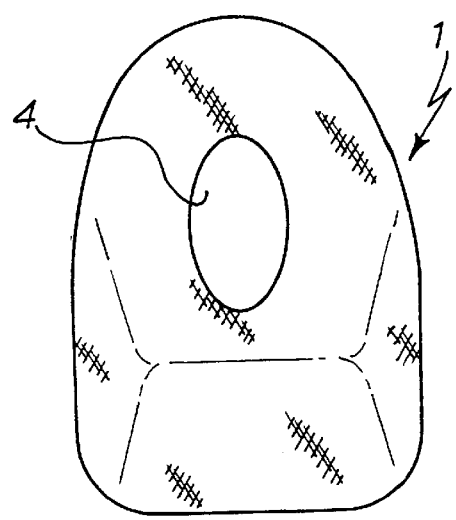
FIG. 2 shows a right side view of the surgical appliance of FIG. 1.

Referring now to FIG. 2, it can be observed that the side 3 of sheath 1 centrally has a circular or oval hole 4 that allows the passage of the bronchia and vessels intended for the ventilation and the perfusion of the pulmonary parenchyma. At rest, this hole should preferably be 9 to 12 cm high and 5 to 7 cm wide. These dimensions may obviously vary depending on the elasticity of sheath 1.

The portion of the sheath above hole 4 has a volume lower than the portion below hole 4. Furthermore, the ratio between the volumes of the portion below and the portion above the hole 4 is suitably greater than the ratio between the volumes of the corresponding basal and apical areas of the lung. Thanks to this arrangement it is possible to compress the apical areas, which are functionally less active, more than the basal ones.

Of course, the size of sheath 1 depends both on the elasticity of the material used for its manufacture and the size and elasticity of the emphysematous lung onto which the sheath is applied. The volume occupied by sheath 1 at rest should be such as to ensure that the emphysematous lung provided with such a sheath reaches the normal theoretical values of the pulmonary capacity of an individual on which a pressure of 10 to 15 cm of water is exerted. Said pressure values, even if remarkably lower than pressures exertable by the thoracic cage under forced or maximum expansion, are indeed enough to prevent, on one hand, the pathological tendency of the emphysematous lung to expand and, on the other hand, the total collapse of the lung itself. Whichever the case, the volume occupied by sheath 1 at rest should not be lower than 2.5 liters in order to ensure a vital minimal expansion of the lung itself.

The surgical appliance according to the present invention can be applied by way of median sternotomy, thoracotomy as well as videothoracoscopy. The patient is intubated with a two-way tube to avoid the ventilation of the lung onto which the surgical appliance is to be applied. This is followed by the complete lysis of pleural adhesions, if any, and the section of the pulmonary ligament up to the lower pulmonary vein. The latter two procedures serve to completely free the mediastinal, diaphragmatic and costal surfaces of the lung, as well as to allow the correct placement of sheath 1 which must be oriented with its upper portion around the apical area of the lung. Such a placement is carried out after the whole lung has passed through hole 4. This is made possible because the lung, excluded from the ventilation, collapses and thereby occupies a volume slightly lower than a fist.

Figure 3:
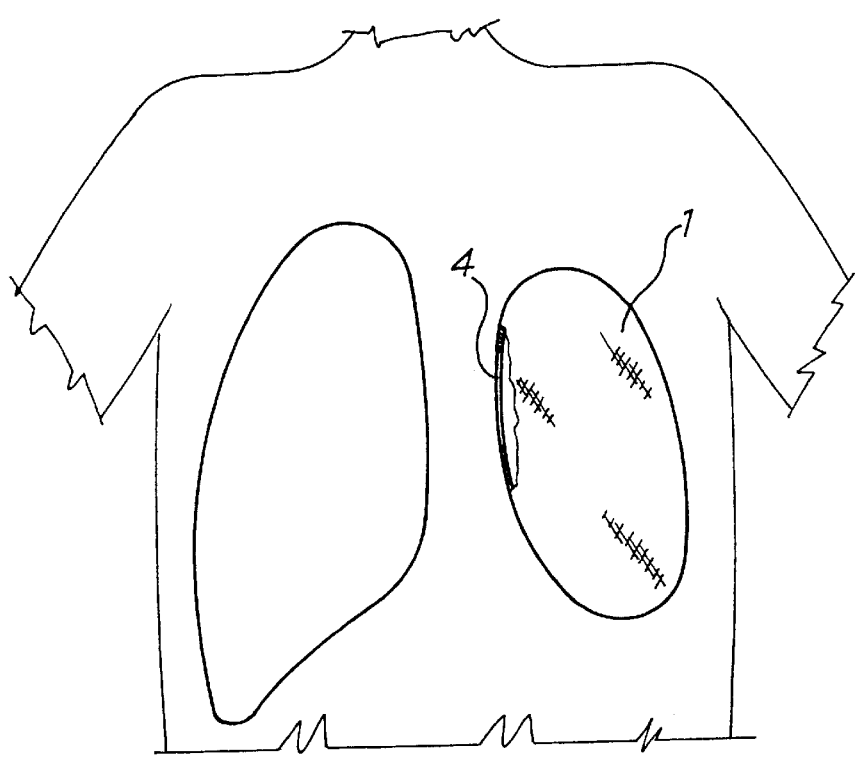
FIG. 3 shows a schematic frontal view of the open thoracic cage of a patient wherein the surgical appliance of FIG. 1 has been applied onto his left lung.

Once sheath 1 is applied around the lung, the latter is ventilated, thereby verifying its correct position within the sheath itself and the amount of its expansion. A lung provided with the surgical appliance according to the present invention is shown in FIG. 3. The figure shows that the left lung, provided with the surgical appliance, occupies a notably reduced volume with respect to the right lung. The volume difference between the two lungs practically corresponds to the amount of pulmonary parenchyma that would have been eliminated by means of removal or plication.

Any change and/or addition can be made by those skilled in the art to the embodiment hereinabove described and illustrated remaining within the scope of the invention. For instances it is clear that the shape of the surgical appliance according to the present invention may change depending upon the particular shape of the lung onto which it is to be applied as well as on the specific emphysematous pathology of said lung.

What is claimed is:

1. A surgical appliance for the treatment of pulmonary emphysema characterized in that said surgical appliance comprises a sheath (1) made up of a biocompatible elastic material, provided with a hole (4) suitable for the passage of the bronchia and vessels of the lung onto which the sheath (1) is to be applied.

2. The surgical appliance according to claim 1, characterized in that the portion of the sheath (1) above the hole (4) occupies a volume lower than the portion below the hole (4).

3. The surgical appliance according to claim 1 or 2, characterized in that the side (3) of the sheath (1) on which the hole (4) is made, is flat.

4. The surgical appliance according to claim 1, 2 or 3, characterized in that the base (2) of the sheath (1) is flat.

* * * * *